(12) United States Patent
Lerner et al.

(10) Patent No.: US 7,579,333 B2
(45) Date of Patent: Aug. 25, 2009

(54) THERAPY USING A COMBINATION OF RALOXIFENE AND ALENDRONATE

(75) Inventors: E. Itzhak Lerner, Petach Tikva (IL); Moshe Flashner-Barak, Petach Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 280 days.

(21) Appl. No.: 11/062,272

(22) Filed: Feb. 18, 2005

(65) Prior Publication Data

US 2005/0282784 A1 Dec. 22, 2005

Related U.S. Application Data

(60) Provisional application No. 60/545,975, filed on Feb. 19, 2004.

(51) Int. Cl.
A61K 31/66 (2006.01)
A61K 31/445 (2006.01)

(52) U.S. Cl. .................. 514/102; 514/108; 514/114; 514/320

(58) Field of Classification Search ................ 514/102, 514/108, 114, 320
See application file for complete search history.

(56) References Cited

U.S. PATENT DOCUMENTS

2001/0051636 A1* 12/2001 Black et al. ................. 514/320
2003/0206954 A1 11/2003 Lerner et al.
2003/0216358 A1 11/2003 Muchmore et al.
2004/0052843 A1* 3/2004 Lerner et al. ................ 424/470

FOREIGN PATENT DOCUMENTS

WO WO 01/28564 4/2001

OTHER PUBLICATIONS

PDR (Physician Desk Reference, http://www.thomsonhc.com.librarian) for Evista tablets).*
PDR (Physician Desk Reference, http://www.thomsonhc.com.librarian) for Fosamax tablets).*
Rocaltrol Oral Solution, Physician's Desk Reference, pp. 2914-2916 (57th Ed., 2003).
Fosamax®, (Alendronate Sodium Tablets) Physician's Desk References, pp. 1996-2003 (57th Ed., 2003).
Evista®, (Raloxefine Hydrochloride) Physician's Desk Reference, pp. 1717-1721 (55th Ed., 2001).
S.C. Abraham et al., "Alendronate-Associated Esophageal Injury: Pathologic And Endoscopic Features" *Modern Pathology*, vol. 12(12), pp. 1152-1157, (1999).
D.Y. Graham et al., "Alendronate gastric ulcers" *Aliment Pharmacol. Ther.*, vol. 13(4), pp. 515-519, (1999).
J.K. Marshall et al., "A randomized controlled trial to assess alendronate-associated injury of the upper gastrointestinal tract" *Aliment Pharmacol. Ther.* vol. 14(11), pp. 1451-1457, (2000).
F.L. Lanza et al., "Placebo-controlled randomized evaluator-blinded endoscopy study of risedronate vs. aspirin in healthy post-menopausal women" *Aliment Pharmacol. Ther.*, vol. 14(12), pp. 1663-1670 (2000).
A.B. Thomson et al., "14-day Endoscopy Study Comparing Risedronate and Alendronate in Post-menopausal Women Stratified by *Helicobacter pylori* Status" *J. Rheumatol.*, vol. 29(9), pp. 1965-1974 (2002).
F. Lanza et al, "Etodolac Compared with Aspirin: An Endoscopic Study of the Gastrointestinal Tracts of Normal Volunteers" *J. Rheumatol.*, vol. 13, pp. 299-303 (1986).
S.N. Elliott et al., "Alendronate Induces Gastric Injury And Delays Ulcer Healing In Rodents" *Life Sciences*, vol. 62(1), pp. 77-91, (1998).
B. J. Gertz et al., "Studies of the oral bioavailability of alendronate" *Clinical Pharmacology & Therapeutics*, vol. 58(3), pp. 288-298, (1995).
U.A. Liberman et al., "Esophagitis and Alendronate" *N. Engl. J. Med.*, vol. 335(8), pp. 1069-1070, (1996).
D.C. Bauer et al., "Upper Gastrointestinal Tract Safety Profile of Alendronate: The Fracture Intervention Trial" *Arch. Intern. Med.*, vol. 160(4), pp. 517-525, (2000).
D. J. Hetzel et al., "Healing and Relapse of Severe Peptic Esophagitis after Treatment with Omeprazole" *Gastroenterology*, vol. 95, pp. 903-912, (1988).
F.L. Lanza et al., "Endoscopic Comparison of Esophageal and Gastroduodenal Effects of Risedronate and Alendronate in Postmenopausal Women" *Gastroentorology*, vol. 119, pp. 631-638, (2000).
R. E. Colina et al., "A New Probable Increasing Cause Of Esophageal Ulceration: Alendronate" *Am. J. Gastroenterology*, vol. 92(4), pp. 704-706, (1997).
D.Y. Graham, "Excess Gastric Ulcers Are Associated With Alendronate Therapy" *Am. J. Gastroenterology*, vol. 93(8), pp. 1395-1396, (1998).
D. Jaspersen, "Drug-Induced Oesophageal Disorders: Pathogenesis, Incidence, Prevention And Management," *Drug Safety*, vol. 22(3), pp. 237-249, (2000).
S. J. Smith et al., "Pill-Induced Esophagitis Caused By Oral Rifampin" *Ann. Pharmocother.*, vol. 33(1), pp. 27-31, (1999).
J. W. Kikendall, "Pill Esophagitis" *J. Clin. Gastroenterol.*, vol. 28(4), pp. 298-305, (1999).
J. H. Lin, "Bisphosphonates: A Review of Their Pharmacokinetic Properties" *Bone*, vol. 18 (2), pp. 75-85, (1996).
A. G. Porras et al., "Pharmacokinetics of Alendronate" *Clin. Pharmacokinet.*, vol. 36, pp. 315-328, (1999).
M. Kleerekoper et al., "Comparative Safety of Bone Remodeling Agents with A Focus on Osteoporosis Therapies" *J. Clin. Pharmacol.*, vol. 41, pp. 239-250, (2001).
A. Cannigia et al., "Effects of 1,25-Dihydroxycholecalciferol on Calcium Absorption in Postmenopausal Osteoporosis" *Clinical Endocrinology*, vol. 11, pp. 99-103, (1979).

(Continued)

*Primary Examiner*—Raymond J Henley, III
(74) *Attorney, Agent, or Firm*—Kenyon & Kenyon LLP

(57) ABSTRACT

Provided are methods of treating bone disease including, but not limited to, osteoporosis, metastatic bone disease, or Paget's disease, by administering a combination of raloxifene and alendronate in a manner that mitigates the formation of ulcerative adverse events.

21 Claims, No Drawings

OTHER PUBLICATIONS

B. L. Riggs et al., "Effect of Long Term Treatment with Calcitriol on Calcium Absorption and Mineral Metabolism in Postmenopausal Osteoporosis" *J. Clin. Endocrinol. Meta.*, vol. 61(3), pp. 457-461, (1985).

I. R. Reid et al., "Long Term Effects of Calcium Supplementation on Bone Loss and Fracture in Post-menopausal Women: A Randomized Controlled Trial" *Am. J. Med.*, vol. 98(4), pp. 331-335, (1995).

Calcitrol, Merck Index pp. 1681-1682 (12th Ed. 1996).

T. Masud et al., "Effects of cyclical etidronate combined with calcitriol versus cyclical etidronate alone on spine and femoral neck bone mineral density in postmenopausal osteoporotic women" *Ann. Rheum. Diseases*, vol. 57, pp. 346-349, (1998).

N. Malvolta et al., "Calcitriol and Alendronate Combination Treatment in Menopausal Women with Low Bone Mass" *Int. J. Tissue React.*, vol. XXI(2), pp. 51-59, (1999).

B. Frediani et al., "Effects Of Combined Treatment With Calcitriol Plus Alendronate On Bone Mass And Bone Turnover In Postmenopausal Osteoporosis-Two Years Of Continuous Treatment" *Clin. Drug Invest.*, vol. 15(3), pp. 235-244, (1998).

R. Nuti et al., "Effect of Treatment with Calcitriol Combined with Low-dosage Alendronate in Involutional Osteoporosis," *Clin. Drug Invest.*, vol. 19(1), pp. 55-61, (2000).

O. Johnell O. et al., "Effects Of Raloxifene (RLX), Alendronate (ALN) And RLX+ALN On Bone Mineral Density (BMD) And Biochemical Markers Of Bone Turnover In Postmenopausal Women With Osteoporosis" *Journal of Bone and mineral Research*, vol. 14, pp. S157, 1100, (1999).

O. Johnell et al., "Additive Effects of Raloxifene and Alendronate on Bone Density and Biochemical Markers of Bone Remodeling in Postmenopausal women with Osteoporosis" *J. Clin. Endocrinol. Metab.*, vol. 87(3), pp. 985-992, (2002).

P. Burckhardt, "Selective Estrogen Receptor Modulators (SERM): neue Substanzen für die Hormonersatztherapie" *Schweizerische Medizinische Wochenschrift*, vol. 129, pp. 1926-1930, (1999).

N. B. Watts, "Treatment of Osteoporosis with Bisphosphonates" *Osteoporosis*, vol. 27 (1), pp. 197-214, (2001).

Patent Abstract, Database EPODOC, NZ 27260895A, May 26, 2000 (US equivalent 2001/0051636).

* cited by examiner

THERAPY USING A COMBINATION OF RALOXIFENE AND ALENDRONATE

CROSS-REFERENCE TO RELATED APPLICATIONS

This application claims the benefit of provisional application Ser. No. 60/545,975, filed Feb. 19, 2004, which is incorporated herein by reference.

FIELD OF INVENTION

The invention encompasses methods of treating bone disease including, but not limited to, osteoporosis, metastatic bone disease, or Paget's disease, by administering a combination of raloxifene and alendronate in a manner that mitigates the formation of ulcerative adverse events.

BACKGROUND OF THE INVENTION

Treatment of osteoporosis, metastatic bone disease, and Paget's disease can benefit from combinations of treatment modalities. These diseases are commonly treated with bis-phosphonates while osteoporosis is also commonly treated with hormone replacement therapy or with selective estrogen receptor modulators. Bis-phosphonates such as alendronate, risedronate, etidronate, zoledronic acid, and tiludronate are commonly prescribed drugs for treatment of these diseases. Despite their benefits, bis-phosphonates suffer from very poor oral bioavailability. Alendronate has less than 1% bioavailability. Gert et al., "Studies of The Oral Bioavailability of Alendronate," *Clinical Pharmacology & Therapeutics*, 1995, 58, 288-298. Alendronate's absorption is inhibited by foods and beverages other than water. Id. When not following the recommended dosing instructions, patients taking alendronate have experienced irritation of the upper gastrointestinal mucosa. Liberman et al., "Esophagitis and Alendronate," *N. Engl. J Med.*, 1996, 335, 1069-70. In rare instances, the irritation associated with the administration of alendronate can be serious. See, FOSAMAX® Warnings, PHYSICIAN'S DESK REFERENCE, pp. 1996-2003 (57$^{th}$ Ed., 2003).

While there are some indications that among the bis-phosphonates, alendronate does not cause ulceration, some literature indicate that alendronate shares this feature with the other bis-phosphonates. See, D. C. Bauer et. al., "Upper gastrointestinal tract safety profile of alendronate: the fracture intervention trial," *Arch. Intern. Med.*, 2000, 160(4), 517-25; Marshall et. al., "A randomized controlled trial to assess alendronate-associated injury of the upper gastrointestinal tract," *Aliment. Pharmacol. Ther.*, 2000, 14(11), 1451-7; Graham et al., "Alendronate gastric ulcers," *Aliment. Pharmacol. Ther.*, 1999, 13(4), 515-9; S. C. Abraham et. al., "Alendronate-associated esophageal injury: pathologic and endoscopic features," *Mod. Pathol.*, 1999, 12(12), 1152-7; Elliott et. al., "Alendronate induces gastric injury and delays ulcer healing in rodents," *Life Sci.*, 1998, 62(1), 77-91; D. Y. Graham, "Excess gastric ulcers are associated with alendronate therapy," *Am. J. gastroenterol.*, 1998, 93(8), 1395-6; and Colina et. al., "A new probable increasing cause of esophageal ulceration: alendronate," *Am. J. Gastroenterol.*, 1997, 92(4), 704-6.

The mechanism of the cause of esophagitis and/or gastritis is not always known, and sometimes it is intrinsic to the chemistry of the particular drug. However, in the case of NSAIDs, bis-phosphonates, and other drugs, there is evidence that implicates contact with the solid form of the drug with ulceration. D. Jasperson, "Drug induced esophageal disorders: pathnogenesis, incidence, prevention and management," *Drug Saf.*, 2000, 22(3), 237-249; Smith et. al., "Pill-induced esophagitis caused by oral rifampin," *Ann. Pharmocother.*, 1999, 33(1), 27-31; J. W. Kikendall, "Pill esophagitis," *J. Clin. Gastroenterol.*, 1999, 28(4), 298-305. Such esophagitis is called pill induced esophagitis or pill esophagitis, and contact gastritis when there is damage to the stomach lining. These forms of mucosal damage can be mitigated by preventing the physical contact of the drug contained in a solid dose formulation with the surface of the mucosa.

Alendronate is best absorbed from in the upper gastrointestinal (GI) tract (duodenum and jejunum). Lin, J. H. "Bisphosphonates: A Review of Their Pharmacokinetic Properties," *Bone*, 1996, 18, 75-85; Porras et al., "Pharmacokinetics of Alendronate," *Clin. Pharmacokinet.*, 1999, 36, 315-328. Alendronate is best absorbed at a pH of ~6. Gert et al., "Studies of The Oral Bioavailability of Alendronate," *Clinical Pharmacology & Therapeutics*, 1995, 58, 288-298.

In addition to bis-phosphonate therapy, options in the treatment of osteoporosis include hormone replacement therapy and calcium supplementation therapy. Kleerekoper et al., "Comparative Safety of Bone Remodeling Agents with A Focus on Osteoporosis Therapies," *J. Clin. Pharmacol.*, 2001, 41, 239. Increased calcium levels can potentially improve the state of bone mineralization in patients with osteoporosis. Over the last thirty years, calcium supplementation, along with vitamin D or vitamin D derivatives such as calcitriol, has been one of the options for treating the problems of osteoporosis. Cannigia et al., "Effects of 1,25-Dihydroxycholecalciferol on Calcium Absorption in Postmenopausal Osteoporosis," *Clin. Endocrinol.*, 1979, 11, 99; Riggs et al., "Effect of Long Term Treatment with Calcitriol on Calcium Absorption and Mineral Metabolism in Postmenopausal Osteoporosis," *J. Clin. Endocrinol. Metab.*, 1985, 61, 457; Reid et al., "Long Term Effects of Calcium Supplementation on Bone Loss and Fracture in Post-menopausal Women, a Randomized Controlled Trial," *Am. J. Med.*, 1995, 98, 331. Calcitriol (1,25-dihydroxyvitamin $D_3$) is a vitamin D derivative that is active in the regulation of the absorption of calcium from the gastrointestinal tract. See, Rocaltrol Oral Solution, Description, PHYSICIAN'S DESK REFERENCE, pp. 2914-2916 (57$^{th}$ Ed., 2003). Calcitriol is the biologically active form of vitamin $D_3$ and stimulates intestinal calcium transport. MERCK INDEX, pp. 1681-1682 (12$^{th}$ Ed. 1997). Calcitriol is used to treat calcium deficiency.

Over the past several years, successful trials have been performed that confirm that there is a synergistic effect in using a combined therapy of calcitriol and bis-phosphonates. Frediani et al., "Effects of Combined Treatment with Calcitriol Plus Alendronate on Bone Mass and Bone Turnover in Postmenopausal Osteoporosis—Two Years of Continuous Treatment," *Clin. Drug Invest.*, 1998, 15, 223; Masud et al., "Effects of Cyclical Etidronate Combined with Calcitriol Versus Cyclical Etidronate Alone on Spine and Femoral Neck Bone Mineral Density in Postmenopausal Women," *Ann. Rheum. Dis.*, 1998, 57, 346; Malvolta et al., "Calcitriol and Alendronate Combination Treatment in Menopausal Women with Low Bone Mass," *Int. J. Tissue React.*, 1999, 21, 51; Nuti et al., "Effect of Treatment with Calcitriol Combined with Low-dosage Alendronate in Involutional Osteoporosis," *Clin. Drug Invest.*, 2000, 19, 56. The goal of the combined therapy trials is to improve therapeutic results and lower the dosage of the two drugs. In these trials the drugs were given individually. International Publication WO 2001/028564 discloses a tablet containing a combination of calcitriol and alendronate in a particular drug ratio range.

Another mode of treatment of osteoporosis is the use of hormone receptor modulators. Raloxifene (Evista®, Eli Lilly), a selective estrogen receptor modulator (SERM), is a benzothiophene non-steroidal estrogen antagonist related to tamoxifen, and is indicated for the prevention and treatment of osteoporosis in post-menopausal women. PHYSICIAN'S DESK REFERENCE, pp. 1717-1721 (55$^{th}$ Ed., 2001).

Decreases in estrogen levels after menopause lead to increases in bone resorption and accelerated bone loss. Raloxifene's activity is mediated by its selective binding to certain estrogen receptors, thus activating or blocking various estrogenic pathways, thereby offsetting the estrogen-induced bone loss. As a result, raloxifene has been shown to increase bone density in the spine and hip, and reduce bone turnover, thus significantly decreasing the incidence of new vertebral fractures by 30-50% among post-menopausal women with osteoporosis. Id. Raloxifene is absorbed rapidly after oral administration. Approximately 60% of the oral dose is absorbed, but due to extensive presystemic glucuronide conjugation (to the metabolites, raloxifene-4-glucuronide, raloxifene-6-glucuronide and raloxifene-6,4-diglucuronide), the oral bioavailability of raloxifene is only 2%.

The combination of hormone receptor modulators and bis-phosphonates has been studied. A study of bone mineral density of one year treatment with alendronate alone, raloxifene alone or the two drugs in combination, showed improved results for the drug combination when compared to either mono-therapy. When dosing 60 mg/day of raloxifene, 10 mg/day of alendronate, or the combined drugs delivered separately in separate dosage forms in 331 patients with osteoporosis for 1 year, improvements in femoral bone mass density were observed for all groups with the combined treatment showing an improvement of 3.7% compared to 2.7% for alendronate alone (P=0.02) and 1.7% for raloxifene alone (P=0.001). Other markers demonstrated improvement in the combination treatment when compared to either treatment alone but did not reach statistical significance when compared to the alendronate alone. O. Johnell et. al. "Additive Effects of Raloxifene and Alendronate on Bone Density and Biochemical Markers of Bone Remodeling in Postmenopausal women with Osteoporosis," *J. Clin. Endocrinol. Metab.*, 2002, 87(3), 985-992.

Although the combination of raloxifene and alendronate demonstrated improved osteoporosis treatment, there is a need for increased dosages of bis-phosphonates in the combination therapy. The invention addresses this need by providing a formulation which mitigates the ulcerative adverse events associated with mucosal contact with bis-phosphonates.

SUMMARY OF THE INVENTION

One aspect the invention is directed towards a pharmaceutical composition comprising at least one bis-phosphonate or pharmaceutically acceptable salt thereof in an amount of at least about 20% higher than a recommended daily dose of the bis-phosphonate, and at least about 30 mg of raloxifene or pharmaceutically acceptable salt thereof, wherein the composition mitigates ulcerative adverse events associated with administration of the bis-phosphonate. Preferably, the composition is in a dosage form. Preferably, the composition is a capsule or tablet of at least one of a powder, granule, pellet, microsphere, or microcapsule.

In a preferred embodiment, the raloxifene is in an amount of about 30 mg to 150 mg, more preferably about 60 mg to 120 mg. Preferably, the raloxifene is in granulated form.

The bis-phosphonate may be in coated or encapsulated form. In one preferred embodiment, the bis-phosphonate and the raloxifene are physically separated from one another. In another preferred embodiment, the bis-phosphonate and the raloxifene are surrounded by an annular body of non-ulcerative material. In another preferred embodiment, the bis-phosphonate is surrounded by an annular body of non-ulcerative material, and the raloxifene is preferably formulated in the annular body. Preferably, the bis-phosphonate is formulated in an inner tablet surrounded by the annular body. The annular body may preferably comprise open axial faces.

Preferably, the bis-phosphonate is alendronate, risedronate, etidronate, zoledronate, clodronate, ibandronate, incadronate, medronate, neridronate, oxidronate, pamidronate, or tiludronate. More preferably, the bis-phosphonate is alendronate.

In a preferred embodiment, the alendronate is in an amount of at least about 15 mg, and the raloxifene is in an amount of at least about 30 mg. Preferably, the alendronate is in an amount of about 15 mg to 70 mg, and the raloxifene is in an amount of about 30 mg to 150 mg. More preferably, the alendronate is in an amount of about 25 mg, and the raloxifene is in an amount of about 60 mg to 120 mg.

Another aspect of the invention is directed towards a method of treating at least one of osteoporosis, metastatic bone disease, or Paget's disease by administering to a mammal in need thereof a therapeutically effective amount of a pharmaceutical composition comprising at least one bis-phosphonate or pharmaceutically acceptable salt thereof in an amount of at least about 20% higher than a recommended daily dose of the bis-phosphonate, and at least about 30 mg of raloxifene or pharmaceutically acceptable salt thereof, wherein the composition mitigates ulcerative adverse events associated with administration of the bis-phosphonate. The composition may be administered as a dosage form, preferably as a daily dosage form.

In a more preferred embodiment, the method of treating at least one of osteoporosis, metastatic bone disease, or Paget's disease comprises administering to a mammal in need thereof a therapeutically effective amount of a pharmaceutical composition comprising about 25 mg of alendronate formulated in an inner tablet surrounded by an annular body of non-ulcerative material with open axial faces, and about 60 mg to 120 mg of raloxifene formulated in the annular body, wherein the composition mitigates ulcerative adverse events associated with administration of alendronate.

DETAILED DESCRIPTION OF THE INVENTION

It has been discovered that a higher dose of alendronate than the standard 10 mg per day, when dosed daily with raloxifene, produces a much improved bone marker profile than a daily dosing of 10 mg of alendronate alone, or a weekly dosing of 70 mg of alendronate.

The invention encompasses a method of administering higher daily doses of bis-phosphonates while avoiding ulcerative adverse events associated with such administration. In particular, the pharmaceutical compositions of the invention comprise bis-phosphonates surrounded by an annular body of non-ulcerative material, such as those embodiments exemplified in U.S. Pub. No. 2003/0206954, incorporated herein by reference to the extent sufficient to enable the invention. As used herein, the term "ulcerative" means causing erosive damage on contact with the mucosa lining. Examples 1 and 2 exemplify mitigation of ulcerative effects by compositions comprising bis-phosphonates surrounded by an annular body of non-ulcerative material.

One aspect the invention is directed towards a pharmaceutical composition comprising at least one bis-phosphonate or pharmaceutically acceptable salt thereof in an amount of at least about 20% higher than a recommended daily dose of the bis-phosphonate, and at least about 30 mg of raloxifene or pharmaceutically acceptable salt thereof, wherein the composition mitigates ulcerative adverse events associated with administration of the bis-phosphonate. The composition may be in a dosage form. Preferably, the composition is administered daily.

The bis-phosphonates may include, but are not limited to, alendronate, risedronate, etidronate, zoledronate, clodronate, ibandronate, incadronate, medronate, neridronate, oxidronate, pamidronate, or tiludronate. The preferred bis-phosphonate is alendronate.

Another aspect of the invention encompasses a method of treating bone related disorders including, but not limited to, osteoporosis, bone metastases, and Paget's disease by administering to a mammal in need thereof a therapeutically effective amount of the composition according to the invention. Bis-phosphonates such as alendronate, risedronate, etidronate, zoledronate, clodronate, ibandronate, incadronate, medronate, neridronate, oxidronate, pamidronate, and tiludronate are the prescribed drugs for treatment of the diseases mentioned above. Osteoporosis is also commonly treated with hormone replacement therapy, hormone receptor modulators, calcium supplementation, and vitamin D derivatives.

Although each treatment focuses on a different biological mechanism or pathway in the organism, the effect of the drugs administered together is additive. In particular, the invention encompasses compositions comprising bis-phosphonates or their acid forms and a selective estrogen receptor modulator, such as raloxifene, in a combination that improves the therapeutic effects of those drugs.

In one embodiment, the bis-phosphonate is in a dosage form that protects the body against ulcerative effects associated with administration of bis-phosphonates. The bis-phosphonate may be in coated or encapsulated form. For example, the dosage form may be prepared by coating the bis-phosphonate, or by formulating the bis-phosphonate into capsules, microcapsules, or microspheres. Coating may be accomplished, for instance, by coating a pellet or tablet comprising the bis-phosphonate. When formulated into capsules, microcapsules, or microspheres, the bis-phosphonate may be in the form of a liquid.

The composition comprising the bis-phosphonate and raloxifene may be in dosage form. Dosage forms include, but are not limited to, capsules, tablets, melt-tablets, sachets, or lozenges. The preferred dosage forms are tablets and capsules. The more preferred dosage form is a tablet. Preferably, the composition is a capsule or tablet comprising two drugs, i.e. bis-phosphonate and raloxifene, formulated as powders, granules, pellets, microspheres, microcapsules, or combinations thereof. In a preferred embodiment, the two drugs are physically separated from one another. The term "physically separated," as used herein, refers to individually contained drugs within one dosage form. For example, two drugs may be formulated as individual pellets within a tablet, individual layers within a tablet, individual microcapsules within a larger capsule, or individually coated granules within a tablet or capsule.

The raloxifene may be formulated with the bis-phosphonate and surrounded by an annular body of non-ulcerative material, or it may be formulated in the annular body surrounding the bis-phosphonate. In one preferred embodiment, the bis-phosphonate and the raloxifene are both surrounded by an annular body of non-ulcerative material.

In another preferred embodiment, the bis-phosphonate is surrounded by an annular body of non-ulcerative material, and the raloxifene is formulated in the annular body. Preferably, the bis-phosphonate is formulated in an inner tablet that is surrounded by the annular body. Also preferably, the annular body comprises open axial faces. An annular body with open axial faces is one that leaves the axial faces recessed and exposed, as exemplified in U.S. Pub. No. 2003/0206954.

The bis-phosphonate is administered at above the recommended daily dosage level to maximize therapeutic efficacy, while the coating protects against the adverse effects associated with administration of bis-phosphonates. As used herein, the term "recommended daily dose" refers to the dosage level for the drug as described in the PHYSICIAN'S DESK REFERENCE ($57^{th}$ Ed. 2003).

In a preferred embodiment, the bis-phosphonate is alendronate. The alendronate may be a free acid, sodium salt, or any other pharmaceutically acceptable salt and/or hydrates thereof. Alendronate is commonly dosed at a daily level of 10 mg per day, and more commonly at weekly level of 70 mg. In one embodiment, the composition comprises at least about 15 mg of alendronate, preferably about 15 mg to 70 mg of alendronate, and more preferably about 15 mg to 50 mg of alendronate. Most preferably, the composition comprises about 25 mg of alendronate.

The composition comprises raloxifene in an amount of at least about 30 mg, preferably about 30 mg to 150 mg, and more preferably about 60 mg to 120 mg. The raloxifene may be admixed with the bis-phosphonate and may be coated in the same manner. In a preferred embodiment, the raloxifene is in granular form, such as a granular powder, and mixed with the bis-phosphonate.

A more preferred embodiment of the invention encompasses a pharmaceutical composition comprising about 25 mg of alendronate formulated in an inner tablet surrounded by an annular body of non-ulcerative material with open axial faces, and about 60 mg to 120 mg of raloxifene formulated in the annular body, wherein the composition mitigates ulcerative adverse events associated with administration of alendronate.

In a most preferred embodiment, the invention encompasses a method of treating at least one of osteoporosis, metastatic bone disease, or Paget's disease by administering to a mammal in need thereof a therapeutically effective amount of a pharmaceutical composition comprising: about 15 mg to 70 mg, most preferably about 25 mg, of alendronate or pharmaceutically acceptable salt thereof formulated in an inner tablet surrounded by an annular body of non-ulcerative material with open axial faces; and about 30 mg to 150 mg, most preferably about 60 mg to 120 mg, of raloxifene or pharmaceutically acceptable salt thereof formulated in the annular body, wherein the composition mitigates ulcerative adverse events associated with administration of alendronate.

The composition encompassed by the invention may further comprise at least one pharmaceutically acceptable excipient. Excipients useful for preparing preferred dosage forms from the composition according to the invention and the instruments necessary to prepare them are described in U.S. Pub. No. 2003/0206954 and U.S. Pub. No. 2004/0052843, which is also incorporated by reference to the extent sufficient to enable the invention.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

Bioavailability of Protected Alendronate Tablet

Examples 1 and 2 summarize a study designed to determine the rate and extent of absorption of alendronate sodium, and effect on the gastrointestinal tract in human subjects upon administration of a solid pharmaceutical dosage form as described in U.S. Pub. No. 2003/0206954.

Method of Producing Protected Alendronate Tablet

Alendronate trihydrate (85.4 g) (TEVA Assia Ltd.) and 2.6 g of xylitol (Danisco Sweeteners OY) were granulated with 20 g water in a Diosna (model P1/6) granulator for 3 min. The granulate was dried at 40° C. for one hour in a fluidized bed dryer and milled through a 0.8 mm screen. The granulate was blended with 11 g crospovidone NF (BASF Pharma) for five minutes. One gram magnesium stearate NF/EP (Mallinkrodt Inc.) was added and the granulate was further blended for an additional 0.5 minutes. The blend was compressed using a Manesty F3 single punch tablet machine fitted with a 5 mm flat beveled punch. The tablet weight was 94.9 mg±1.0% RSD. The hardness of the core tablets was 3-6 kP.

A mixture of 94 g compressible sucrose (Nutab™, DMV International) and 5 g microcrystalline cellulose (Avicel™ pH 10.2, FMC International) were blended for five minutes. One gram magnesium stearate NF/EP (Mallinkrodt Inc.) was added and the mixture was blended for another half a minute.

A Manesty f3 single punch tableting machine was fitted with a spring-biased columnar punch and punch assembly constructed in accordance with U.S. Pub. No. 2003/0206954. The core rod was designed for a 5 mm round core tablet and the die and punches for the outer tablet were designed to produce a round, 9 mm diameter, flat beveled solid pharmaceutical dosage form. The upper punch had a protrusion of diameter 4.5 mm and 1.2 mm in height. The tablet press was operated and the protected tablets were produced. The tablet weight was 474 mg±0.62% RSD and the hardness of the protected tablets was 12-15 kP. The alendronate trihydrate content, expressed as alendronic acid was 66.8 mg±1.38% RSD (82.4 mg alendronate trihydrate being equivalent to 70 mg alendronic acid).

The drug-containing inner tablet was recessed from the surface of the annular body by about 1 mm.

Pharmacokinetic Study

A clinical trial involving twelve (12) human volunteers was conducted to demonstrate the pharmacokinetics of a solid active pharmaceutical dosage form as described in U.S. Pub. No. 2003/0206954 containing 70 mg alendronate. Its pharmacokinetics was compared to that of a commercial 70 mg Fosamax™ tablet of the prior art (Merck & Co, Inc.).

Method

The study was a randomized, open-label, 2-treatment, 2 period, 2 sequence crossover design under fasting conditions. Twelve (12) healthy adult male volunteers, 18-55 years of age were the subjects in the study.

The study was divided into first and second study periods, each of 36 hours duration, with a 14 day "wash-out" period between the study periods. All subjects who completed both study periods were included in the analysis. Subjects were randomly assigned to two groups. One group was administered alendronate via the protected tablet in the first period and administered control Fosamax™ in the second period. The order of administration to the second group was reversed.

In both periods, alendronate was administered in the fasted state. A standardized meal was provided 4 hours after administration. Snacks were provided on a standardized schedule that was the same for all subjects in both study periods. Water was provided ad libitum. In addition, subjects were encouraged to drink at least 200 ml of water at regular intervals during each study period.

The bioavailability of alendronate was determined by measuring the cumulative levels of alendronate excreted in the urine over a 36 hour period following oral ingestion of the test and control tablets (hereafter "$Ae_{0-36}$"). An initial (t=0) urine sample was taken immediately after administration. Urine samples were taken at 11 regularly scheduled points in time over the 36 hour test period. All urine samples were analyzed for alendronate using a validated HPLC-FLR assay.

Results

The main pharmacokinetic parameters obtained from the analyses of urine samples are collected in Table 1.

TABLE 1

| | Pharmacokinetic Parameters | | | | | |
|---|---|---|---|---|---|---|
| | Administration via Protected Tablet | | | Administration via Fosamax ™ (control) | | |
| Parameter | Mean | ±SD | CV (%) | Mean | ±SD | CV (%) |
| $Ae_{0-36}$ (μg) | 113.6 | 77.2 | 67.9 | 102.6 | 36.8 | 36.8 |
| $R_{max}$ (μg/h) | 37.9 | 19.9 | 51.5 | 31.7 | 11.8 | 38.3 |
| $T_{max}$ (h) | 1.4 | 0.9 | — | 1.4 | 0.9 | — |

A comparison of the pharmacokinetic parameters of the protected tablet dosage form with Fosamax™ is provided in Table 2.

TABLE 2

| Comparison of Pharmacokinetics of the Protected Tablet to Fosamax ™ | | |
|---|---|---|
| | $Ae_{0-36}$ (mg) | $R_{max}$ (mg/h) |
| Geometric Mean of Ratio | 0.99 | 1.12 |
| 90% Geometric C.I. | 75.31% to 128.79% | 93.98% to 135.01% |
| Intra-subject C.V. | 37.48% | 24.85% |

Tables 1 and 2 illustrate that alendronate administered as a protected tablet produces essentially the same pharmacokinetic results as Fosamax™. The total amount of the alendronate excreted into urine over 36 hours is essentially the same for both treatments with the maximum rates of excretion (parallel to $C_{max}$ in a pharmacokinetic study of plasma levels of drug) also close.

The profile of excretion into urine was similar for all subjects and in both treatments. The majority of the subjects had a maximum rate of excretion ($R_{max}$) between one and two hours. For five of the subjects, the $R_{max}$ occurred earlier than 1 hour after administration when they took Fosamax™. Four of the subjects experienced a $R_{max}$ in less than an hour when they took the protected tablet. One subject who took Fosamax™ had a $R_{max}$ in the third hour, while two subjects who took the protected tablet had a $R_{max}$ in the third hour.

The total amount of excreted alendronate ranged from 36.9 μg to 158.6 μg when Fosamax™ was administered and from 30.1 µg to 284.4 µg when the protected tablet was administered. In only two subjects was there a greater than twofold difference in the total amount of excreted alendronate. Another subject excreted a very low amount of alendronate regardless of how the alendronate was administered.

The bioavailability of alendronate administered as a protected tablet is equivalent to that of alendronate administered as Fosamax™. However, the dosage form of Fosamax™ does not offer the protection against contact of the alendronate with the mucous membranes of the esophagus and stomach afforded by the protected tablet.

Example 2

Mitigation of Ulcerative Effects

Granulation

Granulation solution was prepared by dissolving and stirring 26 g xylitol (Danisco Sweeteners OY) in 264 g purified water. The mixture was combined with 500 g alendronate sodium monohydrate in a Diosna P-1/6 granulator for 55 seconds with the impellor spinning at 380 rpm without the chopper spinning. The granulate was massed for a further 1 min with the impellor speed of 760 rpm. The wet granulate was transferred to a Diosna Mini Lab FBD (fluidized bed drier) and dried for 40 minutes using an inlet temperature of 70° C. and a fan capacity of 55%. The granulate was dried to a loss on drying (LOD) at 90° C. of <3%. The yield was 516.6 gram or 99.7%. The granulate was transferred to a Quadro Comil mill for milling through a screen with 1143µ holes at an impellor speed of 1300 rpm. The yield of milled granulate was 487.2 g or 99.1%.

The above granulate (434.5 g) were mixed with 110 g Crospovidone NF in an appropriate size polyethylene bag for 5 min. Magnesium stearate NF/EP (5.5 g) (Mallindrodt Inc.) was added to the powder mixture and mixed for a further half minute. The resulting mixture was pressed into tablets using 5.5 diameter flat beveled punches to give tablets weighing 106.4 mg±1.5 mg with a tablet hardness of 4.79±0.5 Kp. The resulting tablet had an equivalent of 70 mg alendronic acid in the form of hydrated sodium salt.

Preparation of Protected Alendronate Tablet

In a 14 l V-mixer, 510 g Nutab™, compressible sugar (DMV International), 1.44 kg Microcelac 100™ USP (sprayed-dried mix of 75 parts lactose monohydrate and 25 parts microcrystalline cellulose) (Meggle Pharma), 510 g Povidone™ USP/BP PVP K-30 or polyvinylpyrrolidone(formulate), 450 g Eudragit RL™ (polymethacrylates) (Degussa), and 60 g Aerosil® R 972 or colloidal silicon dioxide (Degussa), were mixed for 5 min, and 30 g magnesium stearate NF/EP was added and mixed for another 30 sec.

For producing the protected tablet, the powder mixture was compressed on a Manesty LP 39 tablet press fitted with special 9 mm diameter flat beveled upper and lower punches. The lower punch comprised a 0.5 mm central hole in which a sliding core rod was fitted. The upper punch comprises a central protrusion of 5.5 mm diameter and a height of 1.2 mm. Each fully protected tablet weighed 385.6 mg±6.5 mg and had a tablet strength of 8.27±1.0 Kp. The inner tablet was recessed 1.2 mm from both surfaces of the outer tablet. The weight of tablets formed was 720 g.

Dissolution of Alendronate from Protected Tablet

The dissolution of alendronate from the protected tablets was measured in a USP Apparatus III at 37° C. in 250 ml of 0.1N HCl at 10 dips per minute. The results are provided in Table 3.

TABLE 3

Dissolution of Alendronate from Protected Tablet

| Time (Min) | Percent Released |
|---|---|
| 5 | 28 |
| 10 | 36 |
| 20 | 58 |
| 30 | 81 |

Effect of Sodium Alendronate on the Esophageal, Gastric and Duodenal Mucosa

A randomized clinical trial involving 80 healthy volunteers was conducted to assess the protective effect the sodium alendronate formulation described above from injury to the upper gastrointestinal tract. The effects of the protected tablet on the esophageal, gastric and duodenal mucosa were compared to that of a commercial 70 mg Fosamax™ tablet (Merck & Co., Inc.) and also in a parallel placebo-controlled group. Assessment was carried out by an endoscopist-blinded, safety endoscopy study described in Marshall J. K. et al., *A Randomized Controlled Trial to Assess Alendronate-associated Injury of the Upper Gastrointestinal Tract.* 14 Aliment Pharmacol. Ther. 1451-7 (2000); Lanza F. L. et al., *Endoscopic Comparison of Esophageal and Gastric Effects of Risedronate and Alendronate in Postmenopausal Women.* Gastroenterology 119 631-8 (2000) and Thomson A. B. et al., *14-day Endoscopy Study Comparing Risedronate and Alendronate in Post-menopausal Women Stratified by Helicobacterpylori Status.* J. Rheumatol. 29 1965-74 (2002).

Study Design

Eligibility of healthy male and female volunteers was screened by assessing the history, physical examination, laboratory assessment and esophagogastroduodenoscopy (EGD). Criteria for eligibility included: (1) no known history of any medical disorder that would contraindicate administration of the study medication; (2) no erosions or ulcers in the duodenal, gastric and esophageal mucosa at screening endoscopy; (3) no known allergies to alendronate or any inactive component of either the test or reference formulations; (4) not lactose intolerant; (5) non-smokers for the last 6 months; (6) no history of drug or alcohol abuse; and (7) no significant abnormalities in screening physical exam, blood tests (including serum calcium), urinalysis or ECG.

Subjects were excluded if they acknowledged: (1) any abnormality of the esophagus, which may delay esophageal emptying, such as stricture or achalasia; (2) a history of peptic ulcer disease, erosive esophagitis or erosive gastritis outside a research protocol; (3) active *H. pylori* infection as determined by $^{13}$C-urea breath test (Pyloritek™); (4) a history of prior upper gastrointestinal surgery other than cholecystectomy; (5) an inability to stand or sit upright for at least 30 minutes; (6) treatment with any bisphosphonate in the past 3 months; (7) active treatment with an $H_2$-receptor antagonist, proton pump inhibitor, gastroprotective agent, prokinetic agent, systemic corticosteroid, anticoagulant, or systemic antibiotic; (8) use of aspirin or NSAID within 30 days; (9) use of any other prescription medications that could interfere with study endpoints in the opinion of the investigator; (10) use of any over-the-counter medications, including vitamins, laxatives and dietary supplements other than acetaminophen within 7 days; or (11) donation of blood within 30 days or plasma within 14 days.

Eligible subjects were randomized to three parallel treatment groups: (1) protected alendronate sodium 70 mg (N=30); (2) Fosamax™ 70 mg (Merck & Co., Inc.) (N=30); or (3) lactose placebo tablet (N=20). The study subjects took the assigned tablets daily for 14 days. The tablets were taken first thing in the morning with 240 mL water, prior to food intake and in an upright position, which was maintained for at least 30 minutes following dosing. The protected alendronate and placebo tablets were indistinguishable in appearance, and both subjects and study personnel were blinded to treatment allocation.

Method of Assessment

Endoscopies were performed on Day 8 of treatment and repeated on Day 15 of the study by the same endoscopist, who remained blinded to treatment allocation. Gastric and duodenal injuries were scored using the ordinal Lanza scoring scale (See, Lanza F. L., et al, *Etodolac Compared with Aspirin: an Endoscopic Study of the Gastrointestinal Tracts of Normal Volunteers.* 13 J. Rheumatol. 299-303 (1986) and modified Lanza scoring scale [See, Lanza F. L. et al., *Placebo-controlled Randomized Evaluator-blinded Endoscopy Study of Risedronate vs. Aspirin in Healthy Post-menopausal Women.* 14 Aliment Pharmacol. Ther. 1663-70 (2000)] (See, Table 4). Gastric and duodenal ulcers were defined as breaks in the mucosa measuring 3 mm or more with apparent depth.

TABLE 4

Lanza and Modified Lanza Scales for Gastroduodenal Injury

| Grade | Lanza Scale | Modified Lanza Scale |
| --- | --- | --- |
| 0 | No visible lesions | No visible lesions |
| 1 | 1 hemorrhage or erosion | 1-25 hemorrhages |
| 2 | 2-10 hemorrhages or erosions | 1-2 erosions; >25 hemorrhages |
| 3 | 11-25 hemorrhages or erosions | 3-9 erosions |
| 4 | >25 hemorrhages or erosions or any ulcers | >10 erosions or any ulcer |

Esophageal injury was scored using the Hetzel-Dent ordinal scoring scale (Hetzel D. J. et al., *Healing and Relapse of Severe Peptic Esophagitis after Treatment with Omeprazole.* 95 Gastroenterology 903-12 (1988). Subjects with grade 4 or 5 esophageal injury at the Day 8 endoscopy were withdrawn from the protocol. (See, Table 5).

TABLE 5

Hetzel-Dent Scale for Esophageal Injury

| Grade | Description |
| --- | --- |
| 0 | Normal mucosa |
| 1 | Erythema, hyperemia and/or friability |
| 2 | Superficial ulcerations or erosions involving <10% of the mucosal surface area on the last 5 cm of the esophageal squamous mucosa |

TABLE 5-continued

Hetzel-Dent Scale for Esophageal Injury

| Grade | Description |
| --- | --- |
| 3 | Superficial ulcerations or erosions involving 10% to 50% of the mucosal surface area on the last 5 cm of the esophageal squamous mucosa |
| 4 | Deep ulceration anywhere in the esophagus or confluent erosion of >50% of the mucosal surface area on the last 5 cm of the esophageal squamous mucosa |
| 5 | Stricture that precludes passage of the endoscope (if present, discontinue subject from the study) |

The primary study endpoint for each subject was the maximum gastric injury score recorded on Day 8 and Day 15 (Table 10 below). Secondary study endpoints included maximum duodenal and esophageal injury scores at Day 8 and Day 15, the proportions of subjects with gastroduodenal ulcers, and rates of adverse events.

Treatment groups were characterized by analyzing descriptively as means (with standard deviation) for continuous variables and as counts or proportions for categorical variables. Injury scores, ulcer rates and adverse events were cross-tabulated by treatment group. Differences in injury scores among treatment groups were assessed by analysis of variance (ANOVA) with post hoc Bonferroni tests. Results were considered significant if the 2-sided p value was less than 0.05. Differences in ulcer rates between groups were assessed using chi square tests with post hoc Z tests of pairwise comparison. P values were corrected for multiple comparisons by dividing alpha (0.05) by the number of comparisons (Bonferroni correction).

Biostatistical Determination of Sample Size

The planned sample size of 80 subjects (30 on protected alendronate, 30 on Fosamax™ and 20 on placebo) provided 80% power (beta 0.20) to detect a one-grade difference between groups in an ordinal mucosal damage score (alpha 0.05, standard deviation 1.0). Furthermore, this sample provided 80% power (beta 0.20) to detect a 19% difference (alpha 0.05) in the rate of gastric ulcer formation assuming a 20% rate with high-dose Fosamax™.

Results

Study Participants

The baseline characteristics of the 78 study subjects from a total of 110 volunteers screened were summarized in Table 6. The 78 eligible study subjects were randomized to protected alendronate (N=30), Fosamax™ (N=28) or placebo (N=20). Treatment groups were similar, although relatively fewer male patients in placebo group (10.0%, vs. 20.0% on protected alendronate and 25.0% on Fosamax™) and relatively more former smokers patients on Fosamax™ (35.7%, vs. 15.0% on placebo and 13.3% on protected alendronate).

TABLE 6

Baseline Characteristics of Study Participants.

| Characteristics | Alendronate Protected (N = 30) | Fosamax ™ (N = 28) | Placebo (N = 20) | Total (N = 78) |
| --- | --- | --- | --- | --- |
| Age (years) | | | | |
| Mean (SD) | 49.4 (5.8) | 47.6 (5.5) | 47.5 (6.5) | 48.3 (5.9) |
| Median (IQR) | 49.0 (7.8) | 47.5 (8.0) | 47.5 (12.0) | 48.0 (9.3) |
| Range | 23 | 20 | 19 | 23 |

TABLE 6-continued

Baseline Characteristics of Study Participants.

| Characteristics | Alendronate Protected (N = 30) | Fosamax ™ (N = 28) | Placebo (N = 20) | Total (N = 78) |
|---|---|---|---|---|
| Gender N (%) | | | | |
| Female | 24 (80.0) | 21 (75.0) | 18 (90.0) | 63 |
| Male | 6 (20.0) | 7 (25.0) | 2 (10.0) | 15 |
| Race N (%) | | | | |
| Caucasian | 30 (100.0) | 28 (100.0) | 20 (100.0) | 78 (100.0) |
| Other | 0 (0.0) | 0 (0.0) | 0 (0.0) | 0 (0.0) |
| Weight (kg) | | | | |
| Mean (SD) | 75.6 (16.8) | 77.1 (19.3) | 72.5 (12.9) | 75.3 (16.8) |
| Median (IQR) | 74.3 (25.6) | 75.0 (25.6) | 69.8 (21.1) | 73.8 |
| Height (cm) | | | | |
| Mean (SD) | 168.5 (9.0) | 169.8 (7.5) | 167.2 (8.2) | 168.6 (8.2) |
| Median (IQR) | 168.0 (11.3) | 169.0 (7.3) | 165.0 (10.0) | 168.0 |
| Tobacco Use N (%) | | | | |
| Never used | 26 (86.7) | 18 (64.3) | 17 (85.0) | 61 (78.2) |
| Previously used | 4 (13.3) | 10 (35.7) | 3 (15.0) | 17 (21.8) |
| Menopause (females) N (%) | | | | |
| Post menopausal | 12 (40.0) | 8 (28.6) | 7 (35.0) | 27 (34.6) |
| Pre-Menopausal | 12 (40.0) | 13 (46.4) | 11 (55.0) | 36 (46.2) |

Two additional eligible volunteers were enrolled and both were treated with Fosamax™ in accordance with the protocol. One of the additional subjects was female (post-menopausal) and both were former smokers. Neither developed esophageal or duodenal injury. One developed erosive gastritis (Lanza score 2, modified Lanza score 3). The results of a secondary analysis including these subjects did not differ from those of the primary analysis, reported below.

Gastric Injury Scores

Endoscopically, standard gastric Lanza scores revealed no significant difference between Fosamax™ and protected alendronate at Day 8 (Table 7) or Day 15 (Table 8), or in their maximum scores at Day 8 or 15 (Table 9). Both Fosamax™ and protected alendronate groups had significantly higher mean gastric Lanza scores than placebo.

TABLE 7

Gastric Mucosal Injury Scores at Day 8 Endoscopy

| Treatment | Score 0 | Score 1 | Score 2 | Score 3 | Score 4 | Total | Mean Score (SD) |
|---|---|---|---|---|---|---|---|
| Table 7.1: Distribution of gastric Lanza scores at Day 8 | | | | | | | |
| Alendronate Prot | 4 | 3 | 21 | 1 | 1 | 30 | 1.73(0.868) |
| Fosamax ™ | 3 | 3 | 19 | 1 | 2 | 28 | 1.86(0.932) |
| Placebo | 15 | 3 | 2 | 0 | 0 | 20 | 0.35(0.671) |
| Total | 22 | 9 | 42 | 2 | 3 | 78 | |

Anova P < 0.0001. Post hoc Bonferroni: (Alendronate protected vs. Placebo; p < 0.0001), (Fosamax ™ vs. Placebo; p < 0.0001), (Fosamax ™ vs. Alendronate protected; p = 1.000)

| Table 7.2: Distribution of gastric modified Lanza scores at Day 8 | | | | | | | |
|---|---|---|---|---|---|---|---|
| Alendronate Protected | 4 | 9 | 10 | 6 | 1 | 30 | 1.70(1.055) |
| Fosamax ™ | 3 | 5 | 7 | 11 | 2 | 28 | 2.14(1.145) |
| Placebo | 15 | 1 | 2 | 2 | 0 | 20 | 0.55(1.050) |
| Total | 22 | 15 | 19 | 19 | 3 | 78 | |

Anova P < 0.0001. Post hoc Bonferroni: (Alendronate protected vs Placebo; P = 0.001), (Fosamax ™ vs Placebo; P < 0.0001), (Fosamax ™ vs Alendronate protected; p = 0.376)

TABLE 8

Gastric Mucosal Injury Scores at Day 15 Endoscopy

| Treatment | Score 0 | Score 1 | Score 2 | Score 3 | Score 4 | Total | Mean Score (SD) |
|---|---|---|---|---|---|---|---|
| Table 8.1: Distribution of gastric Lanza scores at Day 15 | | | | | | | |
| Alendronate Protected | 9 | 4 | 16 | 1 | 0 | 30 | 1.30(0.952) |
| Fosamax ™ | 7 | 2 | 12 | 1 | 6 | 28 | 1.89(1.423) |
| Placebo | 16 | 1 | 3 | 0 | 0 | 20 | 0.35(0.745) |
| Total | 32 | 7 | 31 | 2 | 6 | 78 | |

Anova p < 0.0001. Post hoc Bonferroni: (Alendronate protected vs. Placebo; p = 0.012), (Fosamax ™ vs. Placebo; p < 0.0001), (Fosamax ™ vs. Alendronate protected; p = 0.134)

| Table 8.2: Distribution of gastric modified Lanza scores at Day 15 | | | | | | | |
|---|---|---|---|---|---|---|---|
| Alendronate Protected | 9 | 12 | 6 | 2 | 1 | 30 | 1.13(1.042) |
| Fosamax ™ | 7 | 5 | 3 | 8 | 5 | 28 | 1.96(1.503) |
| Placebo | 16 | 1 | 1 | 2 | 0 | 20 | 0.45(0.999) |
| Total | 32 | 18 | 10 | 12 | 6 | 78 | |

Anova p < 0.0001. Post hoc Bonferroni: (Fosamax ™ vs Alendronate protected; p = 0.034); (Alendronate protected vs Placebo; p = 0.168); (Fosamax ™ vs Placebo; p < 0.0001)

TABLE 9

Maximum Gastric Mucosal Injury Scores at Day 8 or Day 15 Endoscopy

| Treatment | Score 0 | Score 1 | Score 2 | Score 3 | Score 4 | Total | Mean Score (SD) |
|---|---|---|---|---|---|---|---|
| Table 9.1: Distribution of maximum gastric Lanza scores at Day 8 or Day 15 | | | | | | | |
| Alendronate Protected | 1 | 1 | 25 | 2 | 1 | 30 | 2.033(0.615) |
| Fosamax ™ | 3 | 1 | 16 | 1 | 7 | 28 | 2.286(1.213) |
| Placebo | 13 | 4 | 3 | 0 | 0 | 20 | 0.500(0.761) |
| Total | 17 | 6 | 44 | 3 | 8 | 78 | |

Anova p < 0.0001. Post hoc Bonferroni: (Fosamax ™ vs. Alendronate protected; p = 0.879); (Alendronate protected vs. Placebo; p < 0.0001); (Fosamax ™ vs. Placebo; p < 0.0001)

| Table 9.2: Distribution of maximum gastric modified Lanza scores at Day 8 or Day 15 | | | | | | | |
|---|---|---|---|---|---|---|---|
| Alendronate Protected | 1 | 9 | 10 | 8 | 2 | 30 | 2.033(0.999) |
| Fosamax ™ | 3 | 1 | 5 | 13 | 6 | 28 | 2.643(1.193) |
| Placebo | 13 | 2 | 3 | 2 | 0 | 20 | 0.700(1.081) |
| Total | 17 | 12 | 18 | 23 | 8 | 78 | |

Anova p < 0.0001. Post hoc Bonferroni: (Fosamax ™ vs Alendronate protected; p = 0.111); (Alendronate protected vs Placebo; p < 0.0001); (Fosamax ™ vs Placebo; p < 0.0001)

The mean modified gastric Lanza scores of Day 15 revealed significantly greater gastric injury with Fosamax™ than with protected alendronate (mean difference 0.83, 95% CI 0.05-1.62; p=0.034) (See, Table 8.2). No significant difference between protected alendronate and placebo was seen, but Fosamax™ induced greater injury than placebo (mean difference 1.51, 95% CI 0.64-2.39; p<0.001). Modified mean gastric Lanza scores for Fosamax™ and protected alendronate was not significantly different at the Day 8 endoscopy (See, Table 7.2). Similarly, the maximum scores at Day 8 or 15 were not significantly different (See, Table 9). Both Fosamax™ and protected alendronate were associated with significantly higher mean modified Lanza scores than placebo at the Day 8 endoscopy and in their maximum scores at Day 8 or 15.

In post hoc exploratory analyses, the proportions of subjects with moderate to severe gastric injury (Lanza score 3 or 4) were compared between protected alendronate and Fosamax™ for each time point and for their maximum scores at Day 8 or Day 15 (Table 10).

TABLE 10

Proportions of Subjects with Mild (Lanza score 0-2) vs. Moderate-severe (Lanza score 3-4) Gastric Injury. P values compare Alendronate Protected vs. Fosamax ™

| Treatment | Score 0-2 | Score 3-4 | Total | χ2 p value |
|---|---|---|---|---|
| TABLE 10.1: Distribution of gastric Lanza scores at Day 8 | | | | |
| Alendronate Protected | 28 | 2 | 30 | |
| Fosamax ™ | 25 | 3 | 28 | 0.665 |
| Placebo | 20 | 0 | 20 | |
| Total | 73 | 5 | 78 | |
| TABLE 10.2 Distribution of gastric modified Lanza scores at Day 8 | | | | |
| Alendronate Protected | 23 | 7 | 30 | |
| Fosamax ™ | 15 | 13 | 28 | 0.064 |
| Placebo | 18 | 2 | 20 | |
| Total | 56 | 22 | 78 | |

TABLE 10-continued

Proportions of Subjects with Mild (Lanza score 0-2) vs. Moderate-severe (Lanza score 3-4) Gastric Injury. P values compare Alendronate Protected vs. Fosamax ™

| Treatment | Score 0-2 | Score 3-4 | Total | χ2 p value |
|---|---|---|---|---|
| TABLE 10.3: Distribution of gastric Lanza scores at Day 15 | | | | |
| Alendronate Protected | 29 | 1 | 30 | |
| Fosamax ™ | 21 | 7 | 28 | 0.023 |
| Placebo | 20 | 0 | 20 | |
| Total | 70 | 8 | 78 | |
| TABLE 10.4: Distribution of gastric modified gastric Lanza scores at Day 15 | | | | |
| Alendronate Protected | 27 | 3 | 30 | |
| Fosamax ™ | 15 | 13 | 28 | 0.003 |
| Placebo | 18 | 2 | 20 | |
| Total | 60 | 18 | 78 | |
| TABLE 10.5: Distribution of maximum gastric Lanza scores at Day 8 or 15 | | | | |
| Alendronate Protected | 27 | 3 | 30 | |
| Fosamax ™ | 20 | 8 | 28 | 0.098 |
| Placebo | 20 | 0 | 20 | |
| Total | 67 | 11 | 78 | |
| TABLE 10.6: Distribution of maximum modified gastric Lanza scores at Day 8 or 15 | | | | |
| Alendronate Protected | 20 | 10 | 30 | |
| Fosamax ™ | 9 | 19 | 28 | 0.009 |
| Placebo | 18 | 2 | 20 | |
| Total | 47 | 31 | 78 | |

In almost all comparisons, a trend in favor of protected alendronate was observed. Significant benefits in favor of protected alendronate were noted at Day 15 [standard (See, Table 10.3) and modified (See, Table 10.4)] Lanza scores) and for Day 8 or 15 maximum modified Lanza score (See, Table 10.6). These results suggest that protected alendronate was less likely than Fosamax™ (33.3% vs. 67.9%; p<0.01) to cause moderate to severe gastric injury (Lanza score 3 or 4). In addition, subjects on protected alendronate were less likely to develop gastric ulcers than those on Fosamax™ (3.3% vs. 21.4%; p=0.03). No ulcers developed among subjects randomized to placebo.

Duodenal Injury Scores

Duodenal Lanza scores did not differ among the treatment groups at any time-point assessed (Table 11, Table 12 and Table 13).

TABLE 11

Duodenal Mucosal Injury Scores at Day 8 Endoscopy

| Treatment | Score 0 | Score 1 | Score 2 | Score 3 | Score 4 | Total | Mean Score (SD) |
|---|---|---|---|---|---|---|---|
| Table 11.1: Distribution of duodenal Lanza scores at Day 8 | | | | | | | |
| Alendronate Protected | 29 | 0 | 1 | 0 | 0 | 30 | 0.07(0.365) |
| Fosamax ™ | 23 | 2 | 3 | 0 | 0 | 28 | 0.29(0.659) |
| Placebo | 19 | 1 | 0 | 0 | 0 | 20 | 0.05(0.224) |
| Total | 71 | 3 | 4 | 0 | 0 | 78 | |
| Table 11.2: Distribution of duodenal modified Lanza scores at Day 8 | | | | | | | |
| Alendronate Protected | 29 | 1 | 0 | 0 | 0 | 30 | 0.03(0.183) |
| Fosamax ™ | 23 | 2 | 1 | 1 | 1 | 28 | 0.39(0.994) |
| Placebo | 19 | 1 | 0 | 0 | 0 | 20 | 0.05(0.224) |
| Total | 71 | 4 | 1 | 1 | 1 | 78 | |

TABLE 12

Duodenal Mucosal Injury Scores at Day 15 Endoscopy

| Treatment | Score 0 | Score 1 | Score 2 | Score 3 | Score 4 | Total | Mean Score (SD) |
|---|---|---|---|---|---|---|---|
| Table 12.1: Distribution of duodenal Lanza scores at Day 15 | | | | | | | |
| Alendronate Protected | 28 | 1 | 1 | 0 | 0 | 30 | 0.10(0.403) |
| Fosamax ™ | 24 | 1 | 3 | 0 | 0 | 28 | 0.25(0.645) |
| Placebo | 18 | 1 | 1 | 0 | 0 | 20 | 0.15(0.489) |
| Total | 70 | 3 | 5 | 0 | 0 | 78 | |
| Table 12.2: Distribution of duodenal modified Lanza scores at Day 15 | | | | | | | |
| Alendronate Protected | 28 | 1 | 1 | 0 | 0 | 30 | 0.10(0.403) |
| Fosamax ™ | 24 | 2 | 0 | 2 | 0 | 28 | 0.29(0.810) |

TABLE 12-continued

Duodenal Mucosal Injury Scores at Day 15 Endoscopy

| Treatment | Score 0 | Score 1 | Score 2 | Score 3 | Score 4 | Total | Mean Score (SD) |
|---|---|---|---|---|---|---|---|
| Placebo | 18 | 0 | 1 | 1 | 0 | 20 | 0.25(0.786) |
| Total | 70 | 3 | 2 | 3 | 0 | 78 | |

TABLE 13

Maximum Duodenal Mucosal Injury Scores at Day 8 or Day 15 Endoscopy

| Treatment | Score 0 | Score 1 | Score 2 | Score 3 | Score 4 | Total | Mean Score (SD) |
|---|---|---|---|---|---|---|---|
| Table 13.1: Distribution of maximum duodenal Lanza scores at Day 8 or Day 15 | | | | | | | |
| Alendronate Protected | 27 | 1 | 2 | 0 | 0 | 30 | 0.167(0.531) |
| Fosamax ™ | 22 | 2 | 4 | 0 | 0 | 28 | 0.357(0.731) |
| Placebo | 18 | 1 | 1 | 0 | 0 | 20 | 0.150(0.489) |
| Total | 67 | 4 | 7 | 0 | 0 | 78 | |
| Table 13.2: Distribution of maximum duodenal modified Lanza scores at Day 8 or Day 15 | | | | | | | |
| Alendronate Protected | 27 | 2 | 1 | 0 | 0 | 30 | 0.133(0.434) |
| Fosamax ™ | 22 | 3 | 0 | 2 | 1 | 28 | 0.464(1.071) |
| Placebo | 18 | 0 | 1 | 1 | 0 | 20 | 0.250(0.786) |
| Total | 67 | 5 | 2 | 3 | 1 | 78 | |

Esophageal Injury Scores

Esophageal Hetzel-Dent scores did not differ among the treatment groups at any time-point assessed (See, Table 14, Table 15 and Table 16).

TABLE 14

Esophageal Mucosal Injury Scores at Day 8 Endoscopy
Table 14.1: Distribution of esophageal Hetzel-Dent scores at Day 8

| Treatment | Score 0 | Score 1 | Score 2 | Score 3 | Score 4 | Score 5 | Total | Mean Score (SD) |
|---|---|---|---|---|---|---|---|---|
| Alendronate Protected | 27 | 1 | 2 | 0 | 0 | 0 | 30 | 0.17(0.531) |
| Fosamax ™ | 25 | 1 | 2 | 0 | 0 | 0 | 28 | 0.18(0.548) |
| Placebo | 19 | 1 | 0 | 0 | 0 | 0 | 20 | 0.05(0.224) |
| Total | 71 | 3 | 4 | 0 | 0 | 0 | 78 | |

TABLE 15

Esophageal Mucosal Injury Scores at Day 15 Endoscopy
Table 15.1: Distribution of esophageal Hetzel-Dent scores at Day 15

| Treatment | Score 0 | Score 1 | Score 2 | Score 3 | Score 4 | Score 5 | Total | Mean Score (SD) |
|---|---|---|---|---|---|---|---|---|
| Alendronate Protected | 28 | 1 | 1 | 0 | 0 | 0 | 30 | 0.10(0.403) |
| Fosamax ™ | 27 | 1 | 0 | 0 | 0 | 0 | 28 | 0.04(0.189) |
| Placebo | 20 | 0 | 0 | 0 | 0 | 0 | 20 | 0.00(0.000) |
| Total | 75 | 2 | 1 | 0 | 0 | 0 | 78 | |

TABLE 16

Maximum Esophageal Mucosal Injury Scores at Day 8 or Day 15 Endoscopy
Table 16.1: Distribution of maximum esophageal Hetzel-Dent scores at Day 8 or Day 15

| Treatment | Score 0 | Score 1 | Score 2 | Score 3 | Score 4 | Score 5 | Total | Mean Score (SD) |
|---|---|---|---|---|---|---|---|---|
| Alendronate Protected | 26 | 1 | 3 | 0 | 0 | 0 | 30 | 0.233(0.626) |
| Fosamax ™ | 24 | 2 | 2 | 0 | 0 | 0 | 28 | 0.214(0.568) |
| Placebo | 19 | 1 | 0 | 0 | 0 | 0 | 20 | 0.050(0.224) |
| Total | 69 | 4 | 5 | 0 | 0 | 0 | 78 | |

Gastroduodenal Ulcers

Gastric ulcer was identified in one subject randomized to protected alendronate at Day 8 but not at Day 15 (Table 17). Gastric ulcers were seen in 2 subjects randomized to Fosamax™ at Day 8 and in 5 subjects on Fosamax™ at Day 15. As one subject had an ulcer at Day 8 and Day 15, the total number of subjects on Fosamax™ found to have a gastric ulcer was 6. The cumulative rate of ulcer formation on protected alendronate was significantly lower than that seen on Fosamax™ (21.4% vs. 3.3%, p=0.015). No ulcers developed among patients randomized to placebo. No duodenal ulcers were seen in any treatment group.

TABLE 17

Prevalence of gastric ulcers at Day 8 and Day 15 endoscopy

| | Day 8 | | | Day 15 | | | Day 8 or Day 15 | | |
|---|---|---|---|---|---|---|---|---|---|
| Ulcers (n) | A.P* | Fosamax ™ | Placebo | A.P. | Fosamax ™ | Placebo | A.P. | Fosamax ™ | Placebo |
| 0 | 29 | 26 | 20 | 30 | 23 | 20 | 29 | 22 | 20 |
| 1 | 1 | 2 | 0 | 0 | 5 | 0 | 1 | 6 | 0 |
| χ2 P-value | | 0.440 | | | 0.008 | | | 0.015 | |

*A.P. = Alendronate Protected

Adverse Events

The distribution of adverse events reported by patients in each treatment group is summarized in Table 18. No serious adverse events (SAE) were reported. Overall, adverse events were reported by 25/30 subjects randomized to protected alendronate (83.3%), 24/28 on Fosamax™ (85.7%) and 16/20 on placebo (80.0%) (See, Table 18.1). Of the nine adverse events described as severe in Table 18.3, four occurred among subjects randomized to protected alendronate (13.3%), four on Fosamax™ (14.3%), and one on placebo (5.0%).

TABLE 18

Adverse Events

TABLE 18.1:
Distribution of subjects with adverse events by treatment group

| Adverse Events | Alendronate Protected | Fosamax ™ | Placebo | Total |
|---|---|---|---|---|
| Yes | 25 | 24 | 16 | 65 |
| No | 5 | 4 | 4 | 13 |
| Total | 30 | 28 | 20 | 78 |

TABLE 18-continued

Adverse Events

TABLE 18.2:
Distribution of individual adverse events (total 199 reported)

| Reported Adverse Events | Alendronate Protected | Fosamax ™ | Placebo |
|---|---|---|---|
| Abdominal Discomfort | 4 | 5 | 3 |
| Musculoskeletal Pain | 5 | 5 | 3 |
| Gas | 4 | 6 | 5 |

TABLE 18-continued

Adverse Events

| | | | |
|---|---|---|---|
| Blood in Urine | 2 | 3 | 4 |
| Upper Respiratory Infection | 3 | 1 | 1 |
| Constipation | 1 | 0 | 1 |
| Diarrhea | 3 | 4 | 6 |
| Dyspepsia | 8 | 3 | 2 |
| Fatigue | 1 | 3 | 0 |
| Headache | 15 | 13 | 8 |
| Chest Discomfort | 1 | 2 | 0 |
| Nausea | 4 | 4 | 1 |
| Dysphagia | 2 | 1 | 0 |
| Sinus pain | 0 | 0 | 1 |
| Sore Throat | 1 | 1 | 1 |
| Heartburn | 1 | 1 | 1 |
| Drowsiness | 0 | 2 | 0 |
| Dizziness | 0 | 2 | 0 |
| Other | 1 | 2 | 3 |

An adverse event reported more than once by the same subject was counted as one event.

TABLE 18.3: Severity of adverse events

| Severity | Alendronate Protected | Fosamax ™ | Placebo | Total |
|---|---|---|---|---|
| Mild | 38 | 44 | 24 | 106 |
| Moderate | 34 | 30 | 20 | 84 |

TABLE 18-continued

Adverse Events

| | | | | |
|---|---|---|---|---|
| Severe | 4 | 4 | 1 | 9 |
| Total | 76 | 78 | 45 | 199 |

TABLE 18.4: Relationship of study drug to adverse events

| Relationship | Alendronate Protected | Fosamax ™ | Placebo | Total |
|---|---|---|---|---|
| Not Related | 6 | 8 | 6 | 20 |
| Unlikely | 5 | 3 | 7 | 14 |
| Probable | 0 | 0 | 0 | 0 |
| Possible | 65 | 67 | 32 | 164 |
| Definite | 0 | 0 | 0 | 0 |
| Total | 76 | 78 | 45 | 199 |

TABLE 18.5: Action taken due to adverse events

| Severity | Alendronate Protected | Fosamax ™ | Placebo | Total |
|---|---|---|---|---|
| No Action | 48 | 59 | 30 | 137 |
| Specific Concomitant Drug | 28 | 17 | 15 | 60 |
| Treatment | 0 | 0 | 0 | 2 |
| Study Drug Discontinued | 0 | 2 | 0 | 0 |
| Total | 76 | 78 | 45 | 199 |

TABLE 18.6: Outcome of adverse events

| Outcome | Alendronate Protected | Fosamax ™ | Placebo | Total |
|---|---|---|---|---|
| Completely recovered | 75 | 77 | 44 | 196 |
| Recovered with sequelae | 0 | 0 | 0 | 0 |
| Improving | 0 | 0 | 0 | 0 |
| Still present and unchanged | 1 | 1 | 1 | 3 |
| Deteriorated | 0 | 0 | 0 | 0 |
| Death | 0 | 0 | 0 | 0 |
| Total | 76 | 78 | 45 | 199 |

TABLE 18.7: Seriousness of adverse events (Health Canada definition)

| | Alendronate Protected | Fosamax ™ | Placebo | Total |
|---|---|---|---|---|
| Serious | 0 | 0 | 0 | 0 |
| Not Serious | 76 | 78 | 45 | 199 |
| Total | 76 | 78 | 45 | 199 |

No significant difference in the rate of individual adverse events were reported. Dyspepsia was experienced by 8/30 on alendronate protected (26.7%), 3/28 on Fosamax™ (10.7%), and 2/20 on placebo (10.0%). Dysphagia was reported by 2/30 on protected alendronate (6.7%), 1/28 on Fosamax™ (3.6%), and 0/20 on placebo (See, Table 18.2).

No correlation was observed between upper gastrointestinal adverse effects and the presence of an ulcer at endoscopy. Among the seven subjects with an ulcer (one on protected alendronate and six on Fosamax™), two reported dyspepsia (28.6%), two reported abdominal pain (28.6%), one reported dysphagia (14.3%) and one reported heartburn (14.3%).

Example 3

Sheathed Alendronate with Raloxifene as an Outer Sheath

The core tablet is made of alendronate trihydrate (30.5 g, TEVA Assia Ltd.), xylitol (2.6 g, Danisco Sweeteners OY), and microcrystalline cellulose (Avicel pH102, FMC International), which are granulated with water (20 g) in a Diosna (model P1/6) granulator for 3 minutes. The granulate is dried at 40° C. for one hour in a fluidized bed dryer and is milled through a 0.8 mm screen. The screened granulate is blended with crospovidone NF (11 g, BASF Pharma) for five minutes, magnesium stearate NF/EP (1 g, Mallinkrodt Inc.) is added, and the granulate is further blended for an additional 0.5 minutes. The blend is compressed using a Manesty F3 single punch tablet machine fitted with a 5 mm flat beveled punch. The tablet weight is 94.9 mg and the hardness of the core tablet is 3-6 kP.

The annular sheath tablet is a mixture of compressible sucrose (78.4 g, Nutab, DMV International), raloxifene (15.6 g, TEVA Assia Ltd.), and microcrystalline cellulose (5 g, Avicel pH102, FMC International) which are blended for five minutes. Magnesium stearate NF/EP (1 g, Mallinkrodt Inc.) is added and the mixture is blended for an additional 0.5 minute.

A Manesty F3 single punch tableting machine is fitted with a spring-biased columnar punch and punch assembly as described in U.S. Pub. No. 2003/0206954. The core rod is designed for a 5 mm round core tablet and the die and punches for the outer tablet are designed to produce a round, 9 mm diameter, flat beveled solid pharmaceutical dosage form. The upper punch has a protrusion of diameter 4.5 mm and 1.2 mm height. The tablet press is operated and the solid pharmaceutical dosage forms, i.e., sheathed annular tablets, are produced. The total tablet weight is 475 mg and the hardness of the solid pharmaceutical dosage forms is 12-15 kP. The alendronate trihydrate content in the inner sheathed core, expressed as alendronic acid, is 25 mg and the raloxifene content in the outer sheath is 60 mg. The alendronate containing inner tablet is recessed from the surface of the annular sheath by about 1 mm.

Example 4

Administration of the Alendronate-Raloxifene Composition

Four hundred and fifty post menopausal women are dosed for one year with either once weekly alendronate 70 mg and daily with a placebo of "protected" annular sheathed dosage form (Treatment A); once weekly placebo and daily with a "protected" annular sheathed dosage form containing 25 mg alendronate in the inner tablet and 60 mg raloxifene in the annular sheath (Treatment B); or once weekly placebo and daily placebo dosage forms (Treatment C—control). Examples of the "protected" dosage forms may be found in U.S. Pub. No. 2003/0206954.

At baseline, six, and 12 months, bone mineral density (BMD) is measured by dual x-ray absorptiometry. The bone turnover markers serum osteocalcin, bone-specific alkaline phosphatase, and urinary N- and C-telopeptide corrected for creatinine are measured.

All changes in BMD and bone markers at 12 months will be different between placebo and each of the active treatment groups, Treatment A and Treatment B groups. On average, lumbar spine BMD will increase by about 4% from baseline with treatment A and 7% with treatment B, while decreasing 2% with the placebo group. The increase in femoral neck BMD in Treatment A will be about 3% and in Treatment B about 5%. A small decrease will be measured for the placebo treatment group (Treatment C). The changes from baseline to 12 months in bone markers will range from +10 to −15% with Treatment C (placebo), −40 to −60% with Treatment A, and −50 to −85% in Treatment B group. All the differences will reach statistical significance (P=0.005). Treatment B will be shown to be superior to Treatment A.

What is claimed is:

1. A pharmaceutical composition comprising at least one bis-phosphonate or pharmaceutically acceptable salt thereof in an amount of at least about 15 mg wherein the bis-phosphonate is present in an amount of at least about 20% higher than a recommended daily dose for the treatment of osteoporosis, metastatic bone disease, or Paget's disease; and
raloxifene or pharmaceutically acceptable salt thereof wherein the bis-phosphonate and the raloxifene are physically separated from each other, and the composition mitigates ulcerative adverse events associated with administration of the bis-phosphonate.

2. The composition of claim 1, wherein the raloxifene is in an amount of about 30 mg to 150 mg.

3. The composition of claim 1, wherein the raloxifene is in an amount of about 60 mg to 120 mg.

4. The composition of claim 1, wherein the raloxifene is in granulated form.

5. The composition of claim 1, wherein the bis-phosphonate is in coated or encapsulated form.

6. The composition of claim 1, wherein the bis-phosphonate and the raloxifene are surrounded by an annular body of non-ulcerative material.

7. The composition of claim 1, wherein the bis-phosphonate is surrounded by an annular body of non-ulcerative material.

8. The composition of claim 1, wherein the bis-phosphonate is surrounded by an annular body of non-ulcerative material, and the raloxifene is formulated in the annular body.

9. The composition of claim 1, wherein the bis-phosphonate is formulated in an inner tablet surrounded by an annular body of non-ulcerative material.

10. The composition of claim 1, wherein the bis-phosphonate is surrounded by an annular body of non-ulcerative material with open axial faces.

11. The composition of claim 1, wherein the bis-phosphonate is alendronate, risedronate, etidronate, zoledronate, clodronate, ibandronate, incadronate, medronate, neridronate, oxidronate, pamidronate, or tiludronate.

12. The composition of claim 1, wherein the bis-phosphonate is alendronate.

13. The composition of claim 11, wherein the alendronate is in an amount of at least about 15 mg.

14. The composition of claim 11, wherein the alendronate is in an amount of about 15 mg to 70 mg and the raloxifene is in an amount of about 30 mg to 150 mg.

15. The composition of claim 11, wherein the alendronate is in an amount of about 25 mg and the raloxifene is in an amount of about 60 mg to 120 mg.

16. The composition of claim 1, wherein the composition is in a dosage form.

17. The composition of claim 1, wherein the composition is a capsule or tablet of at least one of a powder, granule, pellet, microsphere, or microcapsule.

18. A method of treating at least one of osteoporosis, metastatic bone disease, or Paget's disease by administering to a mammal in need thereof a therapeutically effective amount of a pharmaceutical composition comprising at least about 15 mg of at least one bis-phosphonate or pharmaceutically acceptable salt thereof and wherein the bis-phosphonate is present in an amount of at least about 20% higher than a recommended daily dose of the bis-phosphonate for the treatment of osteoporosis, metastatic bone disease, or Paget's disease; and raloxifene or pharmaceutically acceptable salt thereof, wherein the bis-phosphonate and the raloxifene are physically separated from one another; and the composition mitigates ulcerative adverse events associated with administration of the bis-phosphonate.

19. The method of claim 18, wherein the composition is in a dosage form.

20. The method of claim 18, wherein the composition is administered daily.

21. A method of treating at least one of osteoporosis, metastatic bone disease, or Paget's disease by administering to a mammal in need thereof a therapeutically effective amount of a pharmaceutical composition comprising:
(a) about 25 mg of alendronate or pharmaceutically acceptable salt thereof formulated in an inner tablet surrounded by an annular body of non-ulcerative material with open axial faces; and
(b) about 60 mg to 120 mg of raloxifene or pharmaceutically acceptable salt thereof formulated in the annular body,
wherein the composition mitigates ulcerative adverse events associated with administration of alendronate.

* * * * *

UNITED STATES PATENT AND TRADEMARK OFFICE
CERTIFICATE OF CORRECTION

| | |
|---|---|
| PATENT NO. | : 7,579,333 B2 |
| APPLICATION NO. | : 11/062272 |
| DATED | : August 25, 2009 |
| INVENTOR(S) | : Lerner et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 529 days.

Signed and Sealed this

Fourteenth Day of September, 2010

David J. Kappos
*Director of the United States Patent and Trademark Office*